(12) United States Patent
Runft et al.

(10) Patent No.: US 9,176,079 B2
(45) Date of Patent: Nov. 3, 2015

(54) DEVICE FOR CONTROLLING PHARMACEUTICAL PRODUCTS

(75) Inventors: Werner Runft, Winnenden (DE); Iulian Maga, Ludwigsburg (DE); Jens Schlipf, Freiberg A. N. (DE); Martin Vogt, Schorndorf (DE)

(73) Assignee: Robert Bosch GmbH, Stuttgart (DE)

( * ) Notice: Subject to any disclaimer, the term of this patent is extended or adjusted under 35 U.S.C. 154(b) by 26 days.

(21) Appl. No.: 14/111,660

(22) PCT Filed: Mar. 1, 2012

(86) PCT No.: PCT/EP2012/053545
§ 371 (c)(1),
(2), (4) Date: Oct. 14, 2013

(87) PCT Pub. No.: WO2012/139809
PCT Pub. Date: Oct. 18, 2012

(65) Prior Publication Data
US 2014/0037061 A1 Feb. 6, 2014

(30) Foreign Application Priority Data
Apr. 13, 2011 (DE) .......................... 10 2011 007 276

(51) Int. Cl.
*B07C 5/346* (2006.01)
*G01N 23/18* (2006.01)
(Continued)

(52) U.S. Cl.
CPC ................ *G01N 23/18* (2013.01); *B07C 5/346* (2013.01); *G01N 23/08* (2013.01); *G01N 33/15* (2013.01); *A61J 3/074* (2013.01); *G01N 21/9508* (2013.01)

(58) Field of Classification Search
CPC ... B07C 5/3416; G01N 33/15; G01N 21/9508
USPC ....................................................... 209/589
See application file for complete search history.

(56) References Cited

U.S. PATENT DOCUMENTS 3,390,769 A   7/1968   Tatham et al.
4,117,935 A   10/1978  Richardson et al.
(Continued)

FOREIGN PATENT DOCUMENTS

DE   1054902    4/1959
DE   19819395   10/1999
(Continued)

OTHER PUBLICATIONS

International Search Report for Application No. PCT/EP2012/053545 dated Jul. 17, 2012 (2 pages).

*Primary Examiner* — Howard Sanders
(74) *Attorney, Agent, or Firm* — Michael Best & Friedrich LLP

(57) ABSTRACT

The invention relates to a device (10; 10*a*) for controlling pharmaceutical products (1) in particular, hard gelatin capsules, by means of a radiation source (11) preferably designed as an X-ray source, comprising a storage device (13) which receives the products (1) in an uncontrolled manner, and from which the products (1) are transferred to a transport element (15) in which the products (1) are arranged such that they form at least one row. The products (1) are transported in a clocked manner in the radiation area (25) of the radiation source (11) which exposes the products (1) to radiation, preferably perpendicular to the longitudinal direction thereof. A first stopping device (20) for separating the products (1) in the row is arranged upstream of the radiation source (11) in the direction of transportation (18) of the products (1), and at least one sensor element (28, 28*a*) coupled to an evaluation device (30) captures the radiation which passed through the products (1). According to the invention, at least two products (1) are separated from the row by means of the first stopping device (20) and are simultaneously positioned in the radiation area (25) and the image of the product (1) is captured by means of the at least one sensor element (28; 28*a*).

15 Claims, 3 Drawing Sheets

(51) Int. Cl.
   *G01N 33/15* (2006.01)
   *G01N 23/08* (2006.01)
   *G01N 21/95* (2006.01)
   *A61J 3/07* (2006.01)

(56) References Cited

U.S. PATENT DOCUMENTS 6,162,998 A * 12/2000 Wurst et al. .................. 177/145

2008/0134629 A1 * 6/2008 Schmied et al. .................. 53/55
2012/0207272 A1 * 8/2012 Runft et al. ..................... 378/57

FOREIGN PATENT DOCUMENTS

| | | |
|---|---|---|
| DE | 102010038544 | 4/2011 |
| EP | 0249791 | 12/1987 |
| EP | 2042855 | 4/2009 |
| JP | H0939910 | 2/1997 |
| JP | H09240604 | 9/1997 |

* cited by examiner

DEVICE FOR CONTROLLING PHARMACEUTICAL PRODUCTS

BACKGROUND OF THE INVENTION

The invention relates to a device for controlling pharmaceutical products, in particular, hard gelatin capsules, by means of a radiation source preferably designed as an X-ray source, comprising a storage device which receives the products in an uncontrolled manner, and from which the products are transferred to a transport element in which the products are arranged such that they form at least one row, wherein the products are transported in a clocked manner in the radiation area (25) of the radiation source (11) which exposes the products to radiation, preferably perpendicular to the longitudinal direction thereof, wherein a first stopping device for separating the products in the row is arranged upstream of the radiation source in the direction of transportation of the products and wherein at least one sensor element coupled to an evaluation device captures the radiation which passed through the products.

Such a device is known from the subsequently published German patent application DE 10 2010 038 544 A1 of the applicant. The net weight of filling material located in hard gelatin capsules can, e.g., be determined using the known device with the aid of a radiation source designed as an X-ray source. In addition, the device is suited, e.g., to detecting undesirable foreign particles or the like in the hard gelatin capsules. In one variant to the embodiment disclosed in FIG. 6 of the addressed document, the pharmaceutical products arrive at a shaft-shaped transport device, in which the pharmaceutical products (hard gelatin capsules) are arranged in a row one above the other, from a storage element that accommodates the pharmaceutical products in an uncontrolled manner. In order to be able to separate respectively one pharmaceutical product from the row, a stopping device in the form of a ratchet pawl is provided, with which the respectively lowest hard gelatin capsule of the row can be separated. Only this hard gelatin capsule is evaluated with regard to the properties mentioned above (net weight or foreign particles) by the image of the X-rays on the side of the hard gelatin capsule opposite to the X-ray source being captured by means of an image recording sensor and being supplied to an evaluation device. A disadvantage with the known device is the relatively low output thereof.

SUMMARY OF THE DESCRIPTION

Based on the prior art described, the aim underlying the invention is to further develop a device for controlling pharmaceutical products such that said device exhibits an increase in performance vis-a-vis the prior art. This aim is met according to the invention by a device for controlling pharmaceutical products by virtue of the fact that respectively at least two products are separated from the row by means of the stopping device and are simultaneously positioned in the radiation area and the image of the product is captured by means of the sensor device. At least a doubling of the output results thereby vis-a-vis the prior art.

In one structural embodiment of the invention, in which the at least two products can be separated from the row in a simple manner, it is proposed that the stopping device comprises two stopping elements which can be brought into operative connection with the products in the transport element and which are spaced apart at a distance from one another in the direction of transportation of the products which corresponds to the length of the two products.

In order to be able to use the device for different formats of the products, wherein the formats vary in the length of the respective products, it is additionally proposed that at least one stopping element for adapting the format to the products is disposed so as to be adjustable in the direction of transportation.

By means of the device according to the invention, properties of the products can be determined, which lead to a "good" or, respectively, "bad" evaluation of the products. In order to facilitate in particular a removal of the "bad products", which removes said "bad products" without manual interventions, it is furthermore proposed in a particularly preferred embodiment that a removal device is disposed downstream of the transport device in the direction of transportation downstream of the radiation source.

In order to thereby be able to remove if need be only a single product from a plurality of products previously evaluated in the region of the radiation source, provision is thus made in a preferable manner for two further stopping elements which are consecutively disposed in the direction of transportation to be arranged downstream of the removal device in the region of the transport device, said stopping elements interacting with a distribution element.

The control or evaluation of the properties of the products requires de facto a certain period of time. In order to be able to design as compact a device as possible despite the required period of time, provision is made in a further embodiment of the invention for an intermediate storage element to be located upstream of the distribution element. In said intermediate storage element, the products can thus be stored temporarily so that they do not have to be immediately removed after leaving the region of the radiation source.

In a preferred structural embodiment of the invention, the intermediate storage element is designed as a storage cylinder that is rotated in a stepped manner about an axis, in which preferably a plurality of receiving areas for respectively one product is provided at equal angular distances to one another.

Further advantages, features and details of the invention ensue from the following description of preferred exemplary embodiments as well as with the aid of the drawings.

DETAILED DESCRIPTION

Figure 1:
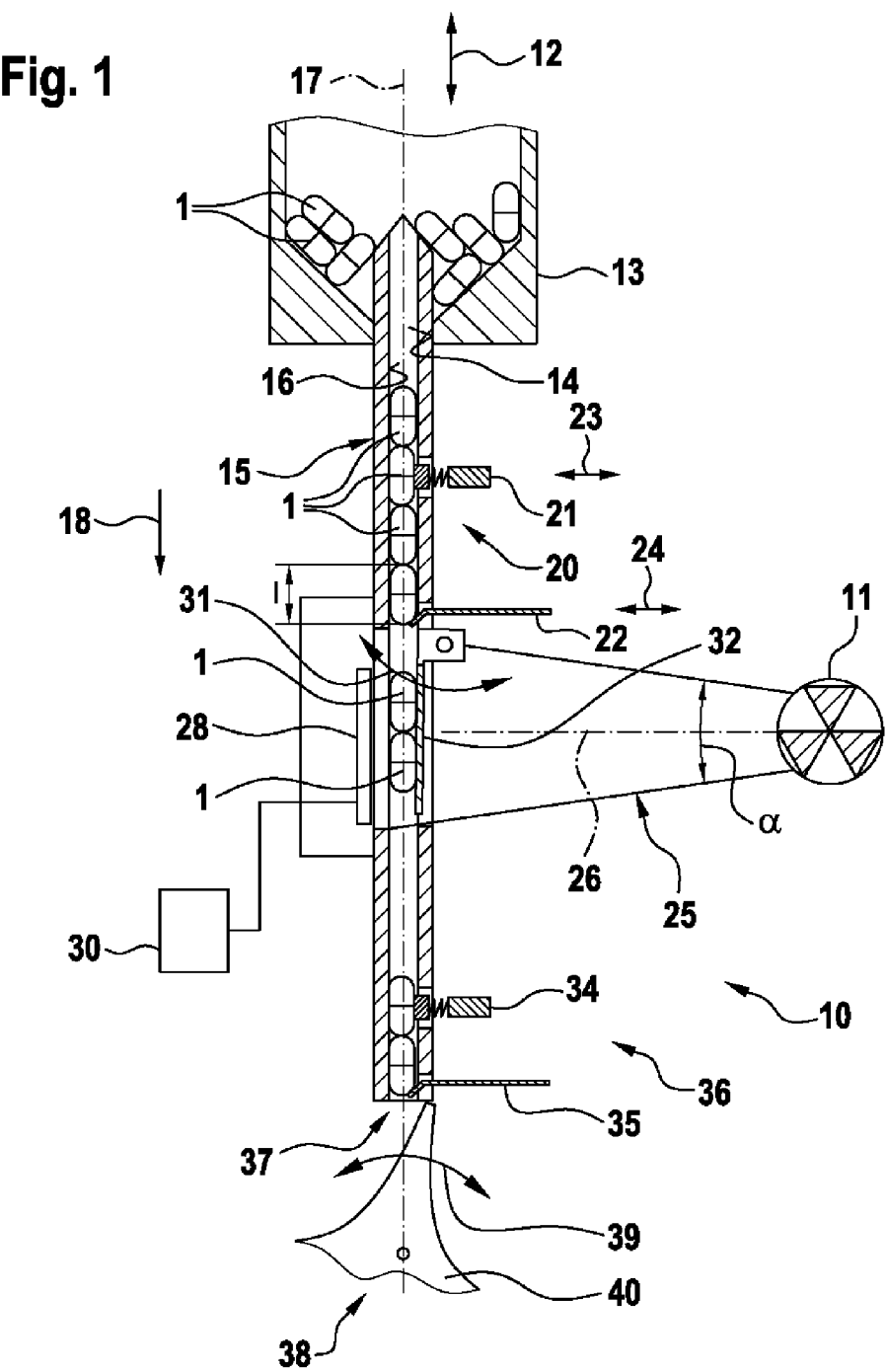
FIG. 1 shows a simplified longitudinal section through a first inventive device for controlling pharmaceutical products by means of an X-ray source.

Identical components or components serving the same function are provided with identical reference numerals in the figures.

A first inventive device 10 for controlling pharmaceutical products, in particular for controlling hard gelatin capsules 1, is depicted in FIG. 1. The hard gelatin capsules 1 are thereby exposed to radiation or, respectively, irradiated by means of an X-ray source 11, and the result of the irradiation is used to assess whether the hard gelatin capsule 1 concerns a "good capsule" or a "bad capsule". By exposing the hard gelatin capsule 1 to radiation, particularly the net weight of the filling material located in the hard gelatin capsule 1 or the presence of foreign particles can be detected or, respectively, ascertained. Refer to the subsequently published German patent application DE 10 2010 038 544 A1 of the applicant for details regarding such a detection or, respectively, evaluation to the extent which it constitutes a part of the present invention.

In addition, it should be mentioned that instead of hard gelatin capsules 1, other pharmaceutical products, such as HPMC capsules, oblong tablets or something similar can be processed using the device 10.

The device 10 comprises a reservoir or storage vessel 13 for the hard gelatin capsules 1 which can move up and down in the direction of the double arrow 12 and in which a large number of hard gelatin capsules 1 are received in an uncontrolled manner. A bore hole 14 is configured in the base area of the storage vessel 13, the former being penetrated by a tubular or shaft-shaped transport element 15. The transport element 15 comprises at least one, however, preferably a plurality of through-holes 16 arranged perpendicularly to the drawing plane of FIG. 1, wherein the diameter of the through-hole 16 is adapted to the diameter of the oblong hard gelatin capsules 1, which have a length 1, in such a way that said hard gelatin capsules 1 can be transported as a row in the through-hole 16. The longitudinal axis 17 of the through-hole 16 is preferably arranged vertically.

The hard gelatin capsules 1 can be transported in the direction of the arrow 18 by means of the transport element 15, said capsules moving in the direction of the arrow 18 solely by the force of their own weight. A stopping device 20 for separating respectively at least two hard gelatin capsules 1 placed one above the other is disposed beneath the storage vessel 13. The stopping device 20 comprises two stopping elements 21, 22 which are consecutively disposed in the direction of transportation of the hard gelatin capsules 1 and which penetrate the wall of the transport element 1 and can be moved in the direction of the double arrows 23, 24 transversely with respect to the longitudinal axis 17 of the transport element 15 by means of drives (not depicted). In the release position of the stopping elements 21, 22, said elements are thereby positioned such that hard gelatin capsules 1 situated in the region of the said stopping elements 21, 22 can move in an unimpeded manner in the direction of the arrow 18. On the other hand, the hard gelatin capsules 1 are held by the respective stopping element 21, 22 in the stopping position of said stopping element 21, 22 by the respective stopping element 21, 22 coming into contact with the relevant hard gelatin capsule 1 and pushing said capsule against the wall of the transport element 15 that is opposite to said stopping element 21, 22.

In order to adapt the format, provision can be made for at least one of the stopping elements 21, 22 to be disposed so as to be adjustable in the direction of the longitudinal axis 17; thus enabling the distance between the two stopping elements 21, 22 to increase in particular in the case of a format adjustment in which the length 1 of the hard gelatin capsules 1 is greater with respect to hard gelatin capsules 1 previously used.

The X-ray source 11 is located at the side beneath the stopping device 20, the former producing a radiation cone 25 having, for example, an angle of aperture a of 30. The center axis 26 of the radiation cone 25 extends preferably, however not imperatively, perpendicularly to the longitudinal axis 17 of the through-hole 16. The transport element 15 consists of a material permeable to X-rays in the region of the radiation cone 25, for example plastic, glass or something similar. On the side of the hard gelatin capsules 1 oppositely disposed to the X-ray source 11, the transport element 15 comprises either a corresponding recess for at least one sensor element 28 or else said transport element 15 likewise consists of a material permeable to X-rays in this region.

The sensor element 28 is designed as an image recording sensor element 28, which records an image of the X-rays of the irradiated hard gelatin capsules 1 and supplies said image to an evaluation device 30. Using an algorithm, the evaluation device 30 checks the hard gelatin capsules 1 irradiated in the region of the sensor element 28 for the property being examined, for example the net weight or the presence of contaminates, foreign particles and the like.

The transport element 15 comprises a clamping element 32 in the form of a clamping plate, which can be pivoted in the direction of the double arrow 31 and which can at least be brought, in the stopping position thereof, into operative connection with the lower of the at least two hard gelatin capsules 1. In so doing, at least the lower of said at least two hard gelatin capsules 1 either presses against the wall of the transport element 15 or else against the sensor element 28 and thus holds those hard gelatin capsules 1, which are being exposed to radiation during an inspection process, in the region of said sensor element 28.

Beneath the X-ray source 11 or, respectively, the sensor element 28, two further stopping elements 34, 35 of an additional stopping device 36 are disposed so as to be spaced apart from the sensor element 28. The further stopping elements 34, 35 are preferably embodied identically to the stopping elements 21, 22; thus enabling reference in this regard to be made to the above description. Each of the hard gelatin capsules 1 located in the region of the additional stopping device 36 can be separated by means of said stopping device 36. Said stopping device 36 serves, in particular, to separate the "bad capsules" from the "good capsules". A removal device 38 located downstream of the outlet 37 of the transport element 15 and having the form of a removal flap 40, which can be pivoted in the direction of the double arrow 39, is used to achieve this objective.

The device described up until now operates as follows: hard gelatin capsules 1 located in the storage vessel 13 are transported via a reciprocating motion of said storage vessel 13 into the through-hole 16 or, respectively, the through-holes 16 of the transport element 15 so that said capsules are queued in a row above the stopping device 20. Respectively at least two hard gelatin capsules 1 placed one above the other in the longitudinal direction are separated from the row by means of the stopping device 20 and transported into the region of the sensor element 28, the clamping device 32 thereby being located in the clamping position thereof. The important aspect here is that the two hard gelatin capsules 1 are thereby released from the other hard gelatin capsules 1 situated above with the exception of the region whereat the two hard gelatin capsules 1 come in contact with one another. As soon as the at least two hard gelatin capsules 1 are situated in the standstill positions thereof in the region of the radiation cone 25 of the X-ray source 11, an image of the irradiated hard gelatin capsule 1 is recorded by means of the sensor element 28 and analyzed or, respectively, evaluated by the evaluation device 30. The clamping device 32 is subsequently pivoted; thus enabling the hard gelatin capsules 1 to be released from the region of the sensor element 28 and to be held for the time being in the region of the additional stopping device 36. Immediately after releasing the two hard gelatin capsules 1 from the region of the sensor element 28, the clamping element 32 is again brought into the stopping position thereof, and therefore the next two hard gelatin capsules 1 can be examined. As soon as the result of the image captured by the sensor element 28 is established by the evaluation device 30, the second stopping device 36 is actuated such that the hard gelatin capsules 1 being examined are either processed further or else discarded depending upon the position of the removal flap 40.

Figure 2:
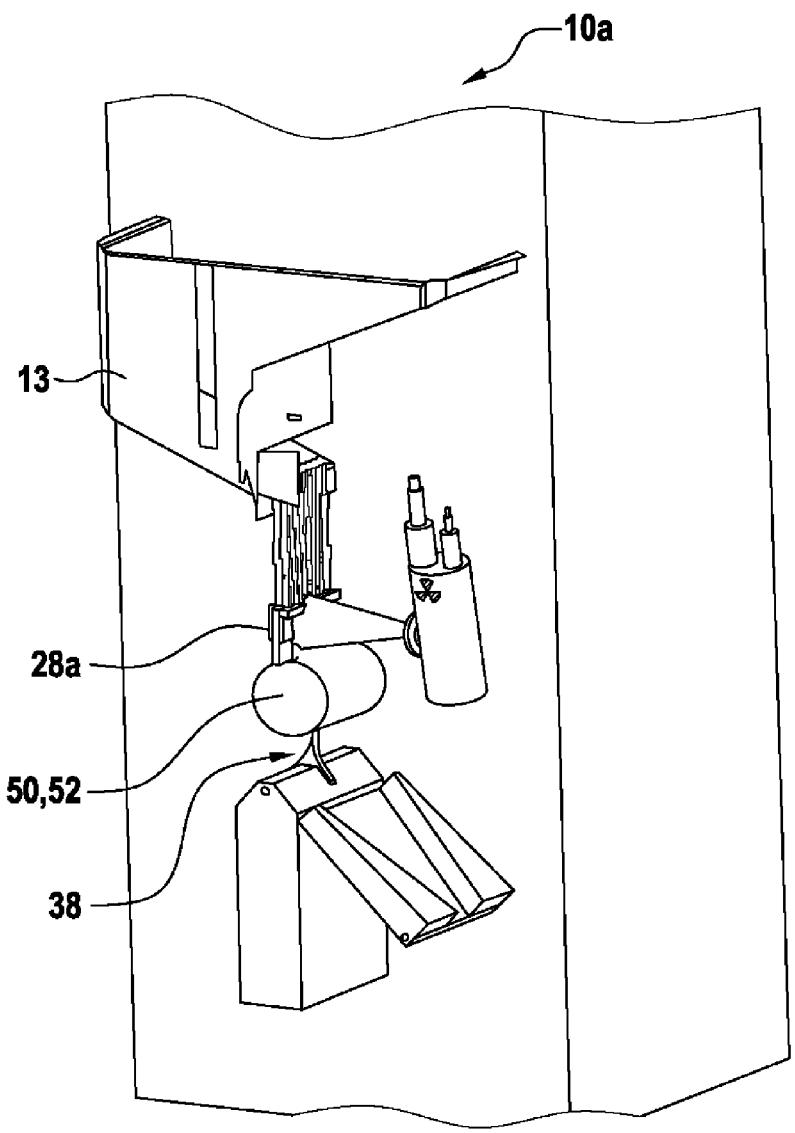
FIG. 2 shows a device which is modified with respect to the device of FIG. 1 in a perspective view and FIG. 3 shows a longitudinal section of a partial region of FIG. 2 in the region of an intermediate storage element.
Figure 3:
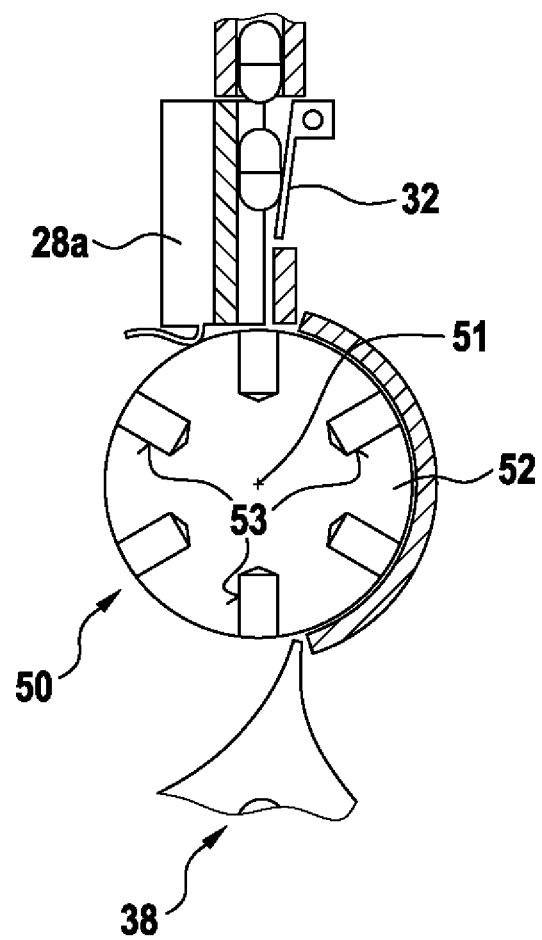

A modified device 10a is depicted in FIGS. 2 and 3. It is important in this context, that an intermediate storage element 50 adjoins the device 10a at the region of the sensor element 28a. The intermediate storage element 50 replaces the second stopping device 36 of the device 10. The intermediate storage element 50 is embodied in the form of a storage cylinder 52 which is rotated in a stepped manner in a horizontal axis of rotation 51. Receiving areas 53 preferably disposed at equal distances from one another are configured on the periphery of the storage cylinder 52, said receiving areas in the form of a bore-hole receiving respectively one single hard gelatin capsule 1. In the pickup position of the intermediate storage element 50 for taking on the respectively lower hard gelatin capsule 1 from the region of the sensor element 28a as well as in the removal position of the hard gelatin capsule 1 from the receiving area 53 of the intermediate storage element 50, the relevant receiving areas 53 are preferably aligned vertically. Said intermediate storage element 50 thus facilitates the intermediate storage of hard gelatin capsules 1 that have already been irradiated particularly when a plurality of receiving areas 53 are available. During the intermediate storage, sufficient time is therefore provided for the evaluation device 30 to be able to determine whether the hard gelatin capsules 1 meet the desired requirements.

The devices 10, 10a described to this point can be modified in a variety of ways without deviating from the concept of the invention. Said inventive concept consists of transporting respectively at least two hard gelatin capsules 1 disposed one above the other into the region of the X-ray source 11 and simultaneously examining the same. It is thus, for example, conceivable to dispense with the stopping device 20 and instead to modify the stopping device 36 to such an extent that three consecutive stopping elements are provided in the direction of transportation of the hard gelatin capsules 1. With such a modification, it is possible, for example, to transfer respectively two hard gelatin capsules 1 into the region of the X-ray source while the lower most stopping element facilitates a transfer of a single capsule to the downstream removal device 38 or, respectively, to the intermediate storage element 50.

The invention claimed is:

1. A device (10; 10a) for controlling pharmaceutical products (1), by means of a radiation source (11), comprising a storage device (13) which receives the products (1) in an uncontrolled manner, and from which the products (1) are transferred to a transport element (15) in which said products (1) are arranged end-to-end such that they form at least one row that defines an axis (17), wherein the products (1) are transported in a clocked manner in a radiation area (25) of the radiation source (11) which exposes said products (1) to radiation, wherein a first stopping device (20) for separating said products (1) in the row is arranged upstream of the radiation source (11) relative to a direction of transportation (18) of said products (1) along the axis (17) and wherein at least one sensor element (28; 28a) coupled to an evaluation device (30) captures radiation which passed through said products (1), characterized in that respectively at least two products (1) are separated from the row in the direction of transportation (18) while remaining on the axis (17) by means of the first stopping device (20) and are simultaneously positioned in the radiation area (25) and an image of the products (1) is captured by means of the at least one sensor element (28; 28a).

2. The device according to claim 1, characterized in that the stopping device (20) comprises two stopping elements (21, 22) which can brought into operative connection with the products (1) in the transport element (15) and which are spaced apart at a distance from one another in the direction of transportation (18) of the products (1) which corresponds to a length (I) of at least two of the products (1).

3. The device according to claim 2, characterized in that at least one of the two stopping elements (21, 22) is disposed so as to be adjustable in the direction of transportation (18).

4. The device according to claim 1, characterized in that a removal device (38) is arranged downstream of the transport element (15) in the direction of transportation (18) downstream of the radiation source (11).

5. The device according to claim 4, characterized in that two further stopping elements (34, 35) consecutively disposed in the direction of transportation (18) are arranged upstream of the removal device (38) in a region of the transport element (15), said stopping elements interacting with a downstream distribution element (40) of the removal device (38).

6. The device according to claim 4, characterized in that an intermediate storage element (50) is arranged upstream of a distribution element (40).

7. The device according to claim 6, characterized in that the intermediate storage element (50) is a storage cylinder (52) which is rotated in a stepped manner about an axis of rotation (51) and in which a plurality of receiving areas (53) for respectively one product (1) is provided at equal angular distances to one another.

8. The device according to claim 7, characterized in that the axis of rotation (51) of the storage cylinder (52) is aligned horizontally and in that the receiving areas (53) are aligned at least approximately vertically in a pickup and removal position of the products (1).

9. The device according to claim 1, characterized in that a clamping element (32) for positioning the at least two products (1) is provided in the radiation area (25).

10. The device according to claim 9, characterized in that the clamping element (32) is designed as a pivotable clamping plate.

11. The device according to claim 1 wherein the pharmaceutical products (1) are hard gelatin capsules.

12. The device according to claim 1 wherein the radiation source (11) is an X-ray source.

13. The device according to claim 1 wherein the radiation source (11) exposes said products (1) to radiation perpendicular to the longitudinal direction thereof.

14. The device according to claim 1 wherein the axis (17) is vertical.

15. The device according to claim 1 wherein the products (1) travel in the direction of transportation (18) solely by the force of their own weight.

* * * * *